(12) United States Patent
Graham et al.

(10) Patent No.: US 12,121,700 B2
(45) Date of Patent: Oct. 22, 2024

(54) OPEN-LOOP INSULIN DELIVERY BASAL PARAMETERS BASED ON INSULIN DELIVERY RECORDS

(71) Applicant: Insulet Corporation, Acton, MA (US)

(72) Inventors: James Graham, Tyngsboro, MA (US); Joon Bok Lee, Acton, MA (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 445 days.

(21) Appl. No.: 17/377,801

(22) Filed: Jul. 16, 2021

(65) Prior Publication Data

US 2022/0023536 A1 Jan. 27, 2022

Related U.S. Application Data

(60) Provisional application No. 63/055,096, filed on Jul. 22, 2020.

(51) Int. Cl.
*A61M 5/00* (2006.01)
*A61M 5/172* (2006.01)
(Continued)

(52) U.S. Cl.
CPC .......... *A61M 5/1723* (2013.01); *G16H 10/60* (2018.01); *G16H 20/17* (2018.01); *G16H 40/67* (2018.01);
(Continued)

(58) Field of Classification Search
CPC ................ A61M 5/1723; A61M 5/142; A61M 5/14276; A61M 5/14248; A61M 5/14244;
(Continued)

(56) References Cited

U.S. PATENT DOCUMENTS

| 303,013 A | 8/1884 | Horton |
|---|---|---|
| 2,797,149 A | 6/1957 | Skeggs |

(Continued)

FOREIGN PATENT DOCUMENTS

| AU | 2015200834 A1 | 3/2015 |
|---|---|---|
| AU | 2015301146 A1 | 3/2017 |

(Continued)

OTHER PUBLICATIONS

US 5,954,699 A, 09/1999, Jost et al. (withdrawn)
(Continued)

*Primary Examiner* — Nathan R Price
*Assistant Examiner* — Tania Ismail
(74) *Attorney, Agent, or Firm* — GOODWIN PROCTER LLP

(57) ABSTRACT

Disclosed are techniques and a device operable to determine a total amount of insulin delivered to the user over a predetermined time period. The total amount of insulin includes a total basal dosage delivered in basal dosages and a total bolus dosage delivered in bolus dosages over the predetermined time period. A proportion of the total amount of insulin delivered to the user provided via the total basal dosage amount over the predetermined time period is calculated. In response determining the proportion of the total amount of insulin attributed to the total basal dosage amount of insulin exceeds a threshold, an average basal dosage to be delivered within a subsequent time period that is approximately equal to the threshold may be determined. An instruction may be generated and output to deliver a modified basal dosage that substantially maintains the average basal dosage over the subsequent time period.

17 Claims, 9 Drawing Sheets

(51) Int. Cl.
  *G16H 10/60* (2018.01)
  *G16H 20/17* (2018.01)
  *G16H 40/67* (2018.01)
  *A61B 5/00* (2006.01)
  *A61B 5/145* (2006.01)
  *A61B 5/1495* (2006.01)
  *A61M 5/142* (2006.01)
  *A61M 5/168* (2006.01)
  *G16H 20/00* (2018.01)
  *G16H 20/10* (2018.01)

(52) U.S. Cl.
  CPC .............. *A61B 5/00* (2013.01); *A61B 5/0002* (2013.01); *A61B 5/14532* (2013.01); *A61B 5/1495* (2013.01); *A61B 5/4836* (2013.01); *A61B 5/4839* (2013.01); *A61B 5/4848* (2013.01); *A61B 5/7225* (2013.01); *A61B 5/725* (2013.01); *A61B 5/7275* (2013.01); *A61M 5/142* (2013.01); *A61M 5/14244* (2013.01); *A61M 5/14248* (2013.01); *A61M 5/14276* (2013.01); *A61M 5/168* (2013.01); *A61M 5/16877* (2013.01); *A61M 2205/00* (2013.01); *A61M 2205/18* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/8206* (2013.01); *A61M 2230/00* (2013.01); *A61M 2230/20* (2013.01); *A61M 2230/201* (2013.01); *A61M 2230/63* (2013.01); *G16H 20/00* (2018.01); *G16H 20/10* (2018.01)

(58) Field of Classification Search
  CPC .............. A61M 5/168; A61M 5/16877; A61M 2230/00; A61M 2230/201; A61M 2230/63; A61M 2230/20; A61M 2205/00; A61M 2205/52; A61M 2205/50; A61M 2205/3561; A61M 2205/502; A61M 2205/18; A61M 2205/3584; A61M 2205/505; A61M 2205/3592; A61M 2205/8206; A61M 2205/581; A61M 2205/582; A61M 2205/583; G16H 20/17; G16H 20/00; G16H 20/10; G16H 10/60; G06F 19/00; G06F 19/3468; G06F 19/3456; A61B 5/00; A61B 5/14532; A61B 5/4839; A61B 5/725; A61B 5/7225; A61B 5/0002; A61B 5/7275; A61B 5/1495; A61B 5/4848; A61B 5/4836

See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |

(56) References Cited

U.S. PATENT DOCUMENTS

| | | |
|---|---|---|
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |

(56) References Cited

U.S. PATENT DOCUMENTS

| | | |
|---|---|---|
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0143864 A1* | 6/2005 | Blomquist ............ G16H 40/60 700/282 |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |

(56) References Cited

U.S. PATENT DOCUMENTS

| | | |
|---|---|---|
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0191063 A1* | 7/2012 | Brauker ............... G16H 40/63 604/504 |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |

(56) References Cited

U.S. PATENT DOCUMENTS

| | | |
|---|---|---|
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | S51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 05110601 A1 | 5/2004 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

(56) References Cited

OTHER PUBLICATIONS

Dassau et al., "Real-Time Hypoglycemia Prediction Suite Using Contineous Glucose Monitoring," Diabetes Care, vol. 33, No. 6, 1249-1254 (2010).
International Search Report and Written Opinion for International Patent Application No. PCT/US17/53262, mailed on Dec. 13, 2017, 8 pages.
Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.
Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker et al., "A Model-Based Agorithm for Blood Gucose Control in Type 1 Diabetic Patients." IEEE Transactions on Biomedical Engineering, 46 (2) 148-147 (1999).
International Search Report and Written Opinion for International Patent Application No. PCT/US2017/015601, mailed May 16, 2017, 12 pages.
International Search Report and Written Opinion for the International Patent Application No. PCT/US2018/018901, mailed on Aug. 6, 2018, 12 pages.
International Search Report and Written Opinion for International Patent Application No. PCT/US2018/052467, mailed Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-hfc-tags-with-an-iphone-app-on-ios-11/>. (Year:2017).
International Search Report and Written Opinion for International Patent Application No. PCT/US2016/063350, mailed on Mar. 27, 2017, 9 pages.
Extended Search Report mailed Aug. 13, 2018, issued in European Patent Application No. 16753053.4, 9 pages.
International Search Report and Written Opinion for International Patent Application No. PCT/US16/18452, mailed on Apr. 29, 2015, 9 pages.
International Preliminary Report on Patentability mailed Aug. 31, 2017, issued in PCT Patent Application No. PCT/US2016/018452, 7 pages.
International Search Report and Written Opinion for International Patent Application No. PCT/US2019/055862, mailed on Mar. 11, 2020.
International Search Report and Written Opinion for Application No. PCT/US2019/030652, Sep. 25, 2019, 19 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator-in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
International Search Report and Written Opinion for the International Patent Application No. PCT/US2022/012896, mailed Apr. 22, 2022, 15 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.

(56) References Cited

OTHER PUBLICATIONS

International Search Report and Written Opinion for the International Patent Application No. PCT/US2020/063326, mailed May 3, 2021, 17 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Preliminary Report on Patentability in PCT/US2021/041954 mailed on Feb. 2, 2023, 10 pages.
European Search Report for the European Patent Application No. 21168591.2, mailed Oct. 13, 2021, 04 pages.
International Search Report and Written Opinion for the International Patent Application No. PCT/US2021/041954, mailed Oct. 25, 2021, 13 pages.
International Search Report and Written Opinion for the International Patent Application No. PCT/US2021/047771, mailed Dec. 22, 2021, 11 pages.
International Search Report and Written Opinion for the International Patent Application No. PCT/US2021/052855, mailed Dec. 22, 2021, 11 pages.
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The Nice-Sugar (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A ""Microbial Contamination of Haemodialysis Catheter Connections"" Journal of Renal Care,European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al, "Multilumen Central Venous Catheters Increase Risk for Catheter-Related Bloodstream Infection: Prospective Surveillance Study".
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS.247VPC).
International Search Report and Written Opinion in PCT/US2008/079641 (Optis.203VPC) dated Feb. 25, 2009.
Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73, 1998.
Berger, "An Enhanced Algorithm for Linear Multivariate Calibration," Analytical Chemistry, vol. 70, No. 3, pp. 623-627, Feb. 1, 1998.
Billman et. al., "Clinical Performance of an in line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol., Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
Anonymous: "Fuzzy control system", Wikipedia, Jan. 10, 2020. URL: https://en.wikipedia.org/w/index.php?title=Fuzzy_control_system&oldid=935091190.

(56) References Cited

OTHER PUBLICATIONS

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

\* cited by examiner

100

| | |
|---|---|
| Determine a total amount of insulin delivered to the user over a predetermined time period | 110 |
| ↓ | |
| Calculate a proportion of the total amount of insulin delivered to the user provided via the total basal dosage amount over the predetermined time period | 120 |
| ↓ | |
| Determine whether the proportion of the total amount of insulin attributed to the total basal dosage amount of insulin exceeds a threshold percentage | 130 |
| ↓ | |
| Calculate an average basal dosage to be delivered within a subsequent time period that is substantially equal to the threshold percentage | 140 |
| ↓ | |
| Generate an instruction to deliver a modified basal dosage that substantially maintains the average basal dosage over the subsequent time period | 150 |
| ↓ | |
| Output the instruction to cause an actuation of a pump mechanism of a medical device to deliver | 160 |

FIG. 1

OPEN-LOOP INSULIN DELIVERY BASAL PARAMETERS BASED ON INSULIN DELIVERY RECORDS

CROSS-REFERENCE TO RELATED APPLICATIONS

This application claims the benefit to U.S. Provisional Application No. 63/055,096, filed Jul. 22, 2020, the entire contents of which are incorporated herein by reference in their entirety.

BACKGROUND

People with Type 1 diabetes (T1D) may utilize specific clinical parameters to manage their insulin deliveries, such as basal programs. However, it is difficult to manually determine the optimal values of these clinical parameters, and patients may compensate for an observed deficiency in certain outcomes by modifying parameters that only tangentially address the issue but cause deficiencies in other areas. For instance, the user may have a basal program that is set to be too low but considers that their resulting hyperglycemia is due to insufficient meal boluses, and thus decides to increase their insulin-to-carbohydrate (I:C) ratios beyond the norm. It would be beneficial to have a "Ground truth" value of at least one fundamental clinical parameter, such as the basal parameter.

Further, the insulin needs of these patients may vary over time. As users begin utilizing automated insulin delivery (AID) systems for a majority of their diabetes care, their open loop parameters may remain untouched—consequently, their clinical parameters may become out of date with the user's true needs based on the changes in their lifestyles or physiology. Accurate and updated open loop parameters will still be needed for these users given that there will be cases where AID is not available, such as sensor unavailability. Methods for utilizing closed loop glucose control outcomes to inform insulin delivery parameters for user's manual control are lacking.

SUMMARY

Disclosed is a device that includes a processor, a memory, a wireless communication device and an artificial pancreas application executable by the processor. The processor may be operable to execute programming code and applications including the artificial pancreas application. The memory may be coupled to the processor and operable to store programming code, an artificial pancreas application and data. The wireless communication device may be operable to wirelessly communicate with a paired device and communicatively coupled to the processor. The artificial pancreas application may be operable to determine a total amount of insulin delivered to the user over the predetermined time period. The total amount of insulin may be a sum of a total basal dosage amount of insulin delivered in the basal dosages over the predetermined time period and a total bolus dosage amount of insulin delivered in the bolus dosages over the predetermined time period. A proportion of the total amount of insulin delivered to the user provided via the total basal dosage amount over the predetermined time period may be determined. The processor may determine whether the proportion of the total amount of insulin attributed to the total basal dosage amount of insulin exceeds a threshold. In response to determining the threshold is exceeded, an average basal dosage to be delivered within a subsequent time period that is approximately equal to the threshold may be determined. An instruction may be generated to deliver a modified basal dosage that substantially maintains the average basal dosage over the subsequent time period. The instruction may be output to cause an actuation of a pump mechanism of the paired device to deliver the modified basal dosage.

Disclosed is a non-transitory computer readable medium embodied with programming code executable by a processor, and the processor when executing the programming code is operable to perform functions, and a process. A processor may be operable to determine a total amount of insulin delivered to the user over the predetermined time period. The total amount of insulin may be a sum of a total basal dosage amount of insulin delivered in the basal dosages over the predetermined time period and a total bolus dosage amount of insulin delivered in the bolus dosages over the predetermined time period. A proportion of the total amount of insulin delivered to the user provided via the total basal dosage amount relative to the sum total amount of insulin delivered over the predetermined time period may be determined. The processor may determine whether the proportion of the total amount of insulin attributed to the total basal dosage amount of insulin exceeds a threshold. In response to determining the threshold is exceeded, an average basal dosage to be delivered within a subsequent time period that is approximately equal to the threshold may be determined. An instruction may be generated to deliver a modified basal dosage that substantially maintains the average basal dosage over the subsequent time period. The instruction may be output to cause an actuation of a pump mechanism of a wearable drug delivery device to deliver the modified basal dosage.

BRIEF DESCRIPTION OF THE DRAWINGS

FIG. 1 illustrates a flowchart of an example of a process for modifying basal insulin dosages related to a diabetes treatment program implemented by one or more of the disclosed examples.

DETAILED DESCRIPTION

Figure 2:
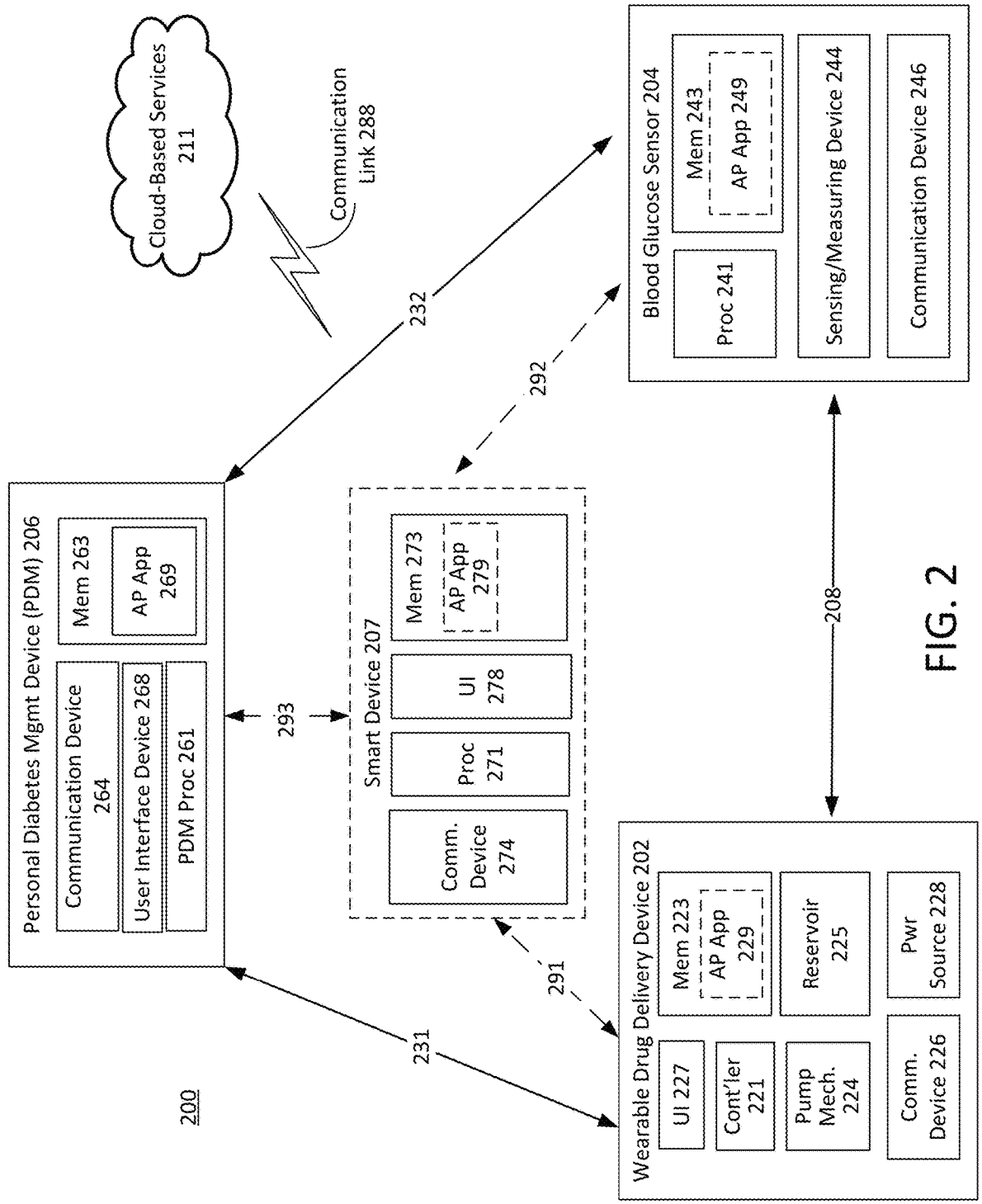
FIG. 2 illustrates a functional block diagram of drug delivery system suitable for implementing the example processes and techniques described herein.

It would be advantageous if automatic insulin delivery (AID) systems, which may use an AID algorithm, were properly tuned to compensate for a user's basal insulin needs. Therefore, the AID systems can determine the users' optimized basal needs following examination of insulin delivery records from automated delivery. Basal insulin profile recommendations can also include elements of time dependence based on the insulin delivery patterns instructed by the AID system, to provide time-dependent basal profiles instead of a constant estimate of the user's basal needs. The following description of the examples provided herein describe techniques and devices that enable optimization of proposed open-loop insulin delivery basal parameters based on insulin delivery records and the utilization of closed-loop glucose control outcomes to inform insulin delivery parameters for a user's manual control.

An example provides a process that may be used with any additional algorithms or computer applications that manage blood glucose levels and insulin therapy. Such algorithms may be referred to as an "artificial pancreas" algorithm-based system, or more generally, an artificial pancreas (AP) application or automatic insulin delivery (AID) algorithm that provides automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. Alternatively, or in addition, an AP application (or AID algorithm) as described herein may be able to establish a target blood glucose value more precisely and may set the target blood glucose value at, for example, 110 mg/dL, or the like. As described in more detail with reference to the examples of FIGS. 1-5, the AP application (or AID algorithm) may utilize the monitored blood glucose measurement values and other information to determine a modified basal dosage that substantially maintains the average basal dosage over the subsequent time period, or the like.

Due to the complicated and dynamic nature of the human body's response to insulin users may end up in a hypoglycemic or hyperglycemic state after being treated with insulin therapy. This outcome is undesirable for many reasons: hypoglycemia creates an immediate risk of a severe medical event (such as a seizure, a coma, or a death) while hyperglycemia creates long term negative health effects as well as the risk of ketoacidosis. Whether a person ends up in one of these states depends on a very complicated combination of many factors and sources of error.

Individuals affected with diabetes have a plethora of complicated decisions to make throughout the day to ensure a user is providing themselves with adequate insulin therapy. An AID system that utilizes AID algorithms and/or an artificial pancreas (AP) application is operable to make many insulin delivery and insulin therapy-related decisions for a user so that the user may live their lives as close to the average non-diabetic individual as possible.

The intersection of closed-loop and open-loop systems is difficult to navigate for most diabetics. In an optimal scenario, a diabetic user obtains half (i.e., 50%) of their total daily insulin from basal delivery of insulin and the other half (i.e., 50%) from bolus deliveries. The basal-delivered insulin as part of a basal program that may be a daily schedule for continuous insulin delivery. The daily schedule may include one or more segments, each defining a basal rate that together cover a 24 hour period. Basal rates are specified in units per hour (U/hr). Alternatively, or in addition, the basal-delivered insulin may be considered background insulin that is used to manage the user's fluctuating needs for insulin in an attempt to maintain the user's blood glucose measurement values within the appropriate range (approximately 70 mg/dL-120 mg/dL for a typical user).

While an optimal scenario provides for a diabetic user obtains half (i.e., 50%) of their total daily insulin from basal delivery of insulin and the other half (i.e., 50%) from bolus deliveries, it may not be possible to regularly achieve such a balance and acceptable variations may occur. The sources of the acceptable variations may be numerous, but the following examples are provided to illustrate possible scenarios that achieve a sufficient balance for users.

In an example a user's insulin needs may vary, and, although the average insulin delivery proportion covered by basal is 50%, a user may have temporary periods where their needs may exceed that amount (which may typically be averaged out by periods when they need less insulin). For example, a user may need 48 U of insulin per day. This translates to an estimated basal need of 2 U/h throughout the day. However, the user's actual insulin need may be 0.5 U/h for the first 12 hours, and 1.5 U/h for the second 12 hours. This still averages to 50% of total daily insulin (TDI) being covered by basal, but the user requires 25% of TDI as basal for first 12 hours, and 75% of TDI as basal for the second 12 hours. Also, some users may ingest significantly more food compared to their physiology—e.g., a 100 lb. person and 250 lb. person may both ingest 300 g of carbohydrates (CHO) per day, in which case the basal insulin needs for the 100 lb. person compared to their total insulin needs may likely be significantly below 50%.

Another source of variations to the diabetes treatment program may be in response to a user's behavior. For example, even if a user would only need 50% of their TDI as basal, the user may neglect to bolus for a significant portion of their meals when using automated insulin delivery. In this case, the automated insulin delivery may deliver 50% of TDI for the user's basal needs, plus another 20% of TDI to cover for the user's bolus needs that were not actually delivered.

So, while an optimal diabetes treatment program may deliver 50% of a user's TDI via basal insulin delivery and 50% via bolus insulin delivery, the above examples of variations from the optimal diabetes treatment program that may alter the responses to the variations by the disclosed examples.

In contrast to the basal dosage, a bolus delivery is administered to cope with large fluctuations in the user's blood glucose measurement values due to, for example, the ingestion of a meal, snack, sugary drink, in response to exercise, or other causes of large fluctuations between blood glucose measurement values. Depending upon a person's lifestyle patterns, this 50-50 split may not be attainable because of their behaviors. However, while attaining this 50-50 split is difficult, the AID algorithm or AP application as described herein may be operable to optimize a user's balance between basal dosages and bolus dosages.

In typical examples, AID systems that utilize an AID algorithm or AP application may be designed with sufficient robustness to provide safe glucose control through their insulin deliveries even if the input parameters may be slightly mistuned, as long as other unknown disturbances are sufficiently compensated (such as meals with accompanying meal boluses). Therefore, these automated insulin delivery records may be utilized by the AID systems to also provide an updated estimate of the user's true basal needs and enable improved optimization of the basal dosage in view of safety constraints around the basal-bolus distribution.

In the following examples, there are two factors that may be utilized to convert records of automated insulin delivery, thereby enabling tuning of the user's basal needs: 1) insulin deliveries separate from meal boluses, and 2) safety constraints using known basal/bolus distributions (e.g., the above mentioned 50-50 basal-bolus dosage distribution).

Details for tuning the basal insulin dosages of a user are described with reference to the examples illustrated in the figures.

Figure 3A:
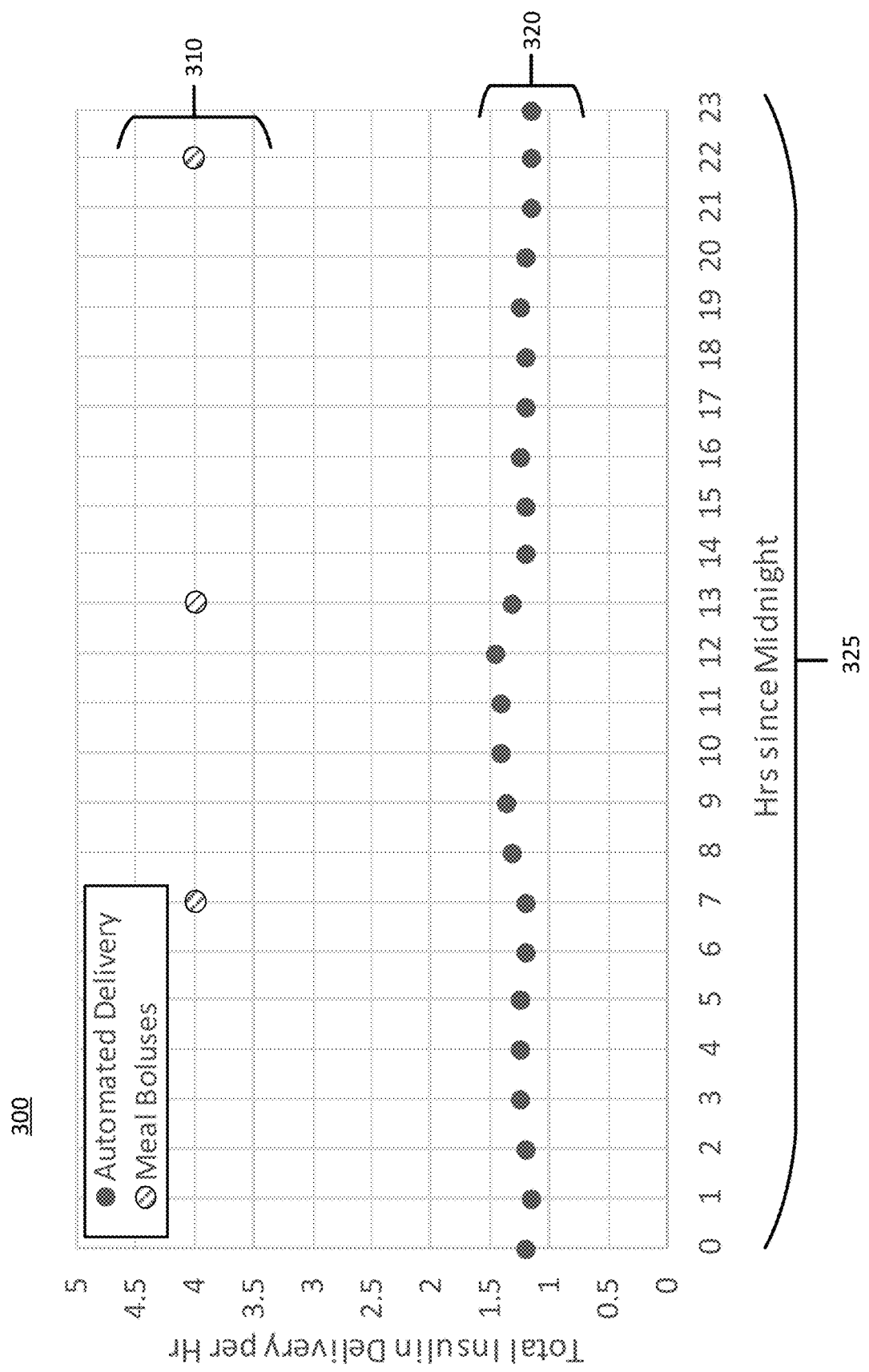
FIG. 3A illustrates an example of basal insulin dosages delivered over a predetermined time period.
Figure 3B:
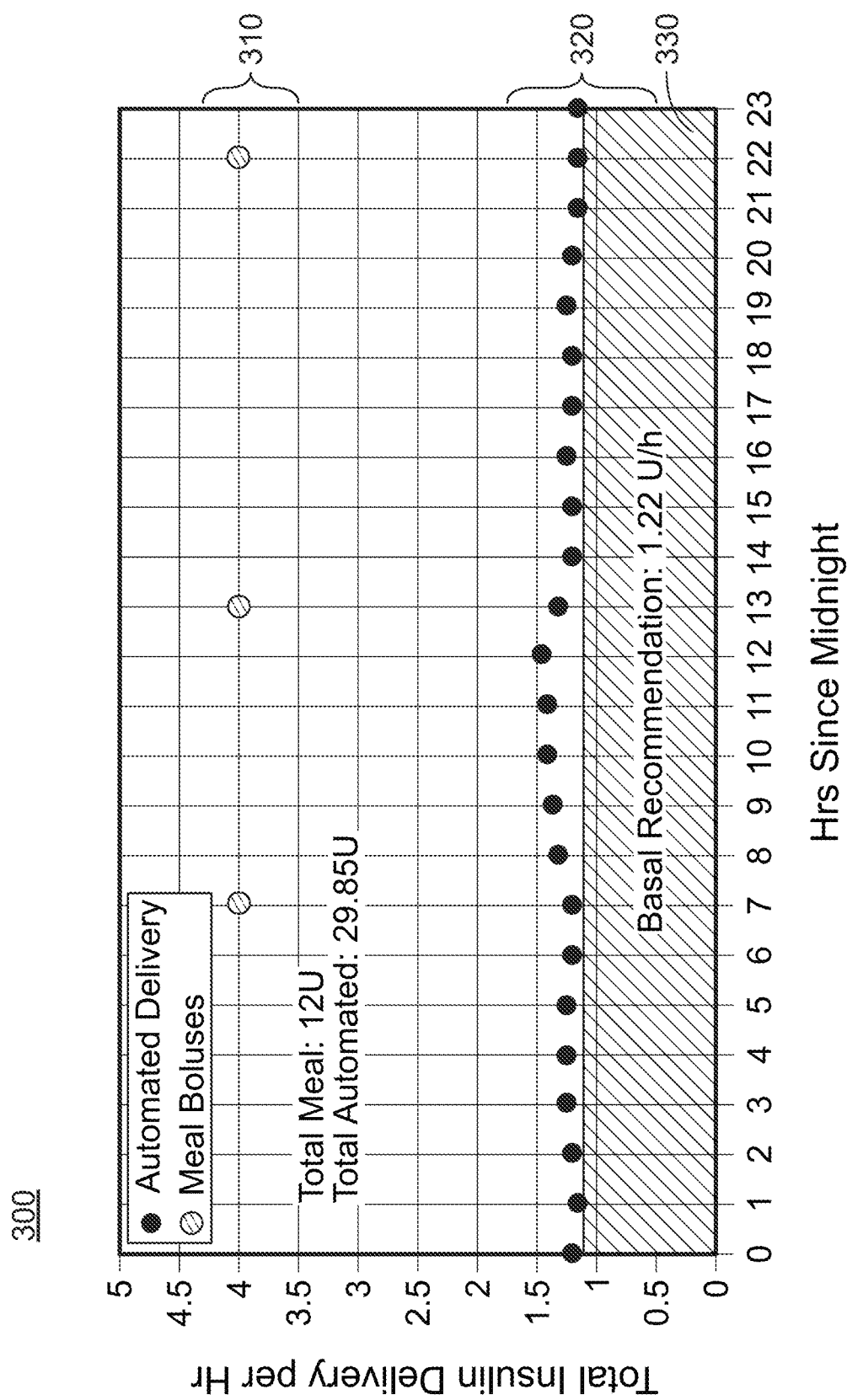
FIG. 3B illustrates a further of an average basal insulin dosage determined based on basal insulin dosages delivered over a predetermined time period of FIG. 3A.

FIG. 1 illustrates an example of a process for modifying basal insulin doses related to a diabetes treatment program implemented by one or more components of the example system below. In the example, a processor may be operable to determine a total amount of insulin delivered to the user over the predetermined time period (110). In the example, the total amount of insulin may be a sum of a total basal dosage amount of insulin delivered in the basal dosages over the predetermined time period and a total bolus dosage amount of insulin delivered in the bolus dosages over the predetermined time period. For example, FIG. 3A shows examples of individual meal boluses 310 (in units of insulin) delivered at approximately mealtimes in the course of a 24 hour day and individual basal dosages 320 (in units of insulin) that are administered over a predetermined time period 325. As shown in FIG. 31, a basal dosage is delivered more frequently over the predetermined time period (e.g., 24 hours) than a bolus dosage. In the example of FIG. 3A, the predetermined time period 325 is 24 hours measured in hourly increments since midnight. FIGS. 3B-5C similarly are also described with reference to a 24 hour predetermined time period. Of course, other time scales may be used, such as 12 hours, 18 hours, 48 hours, 72 hours or the like, for the predetermined time period. FIG. 3B illustrates an example of the total insulin (in units) delivered as individual meal boluses 310 and individual basal dosages 320 and a modified value 330 of the basal dosages may be determined via the process 100 of FIG. 1 as described below with reference to steps 120-150. The total insulin delivered via bolus at mealtimes (labeled "Total Meal") is 12 units (U) and the total insulin delivered as basal doses (labeled "Total Automated") is 29.85 U. In some examples, at 110, the processor may omit amounts of insulin delivered via the bolus dosages and any basal dosages delivered within a preset period of time of delivery of each of the bolus dosages from being included in the total amount of insulin delivered to the user over the predetermined time period. The preset period of time may be set based on user history or be a set period, such as 10-30 minutes, or the like.

In the example process 100 of FIG. 1 at 120, a processor may be operable to calculate a proportion of the total amount of insulin delivered to the user provided via the total basal dosage amount over the predetermined time period. The predetermined time period may be, for example, 24 hours, 48 hours or 72 hours. As shown in FIG. 3B, for example, the total insulin delivered as basal dosages over the predetermined time period was 29.85 U, which equates to an average basal dosage of approximately 1.24 U/hour over the predetermined time period (e.g., 24 hours in this example). The processor may also be operable to determine the proportion of the total amount of insulin delivered in the basal dosages by performing the following calculation: 29.85/(12+29.85)=0.713. The processor may determine that 71.3% of the user's total insulin delivery for the predetermined time period was delivered in the basal dosages.

In response to the calculated proportion (e.g., 0.713 or 71.3%), the processor may be operable to determine whether the proportion of the total amount of insulin attributed to the total basal dosage amount of insulin exceeds a threshold (130). The threshold may be a value that is determined based on clinical data over a number of diabetic patients. For example, the threshold may be determined based on a determination that a user may overdeliver (or underdeliver) insulin by a high percentage compared to the standard amount of 50% of the user's average total daily insulin (TDI) during the course of a predetermined time period (e.g., a day, 24 hours or the like) and by how much (the user over or under delivers). The threshold may be a threshold value, such as the 0.713, a threshold percentage, such as the 71.3%, or the like. In this example, the threshold value may be 0.700, and the process 100 may cause the generation of an indication by the processor that the threshold is exceeded.

In response to determining the threshold is exceeded, the processor may be operable to calculate an average basal dosage to be delivered within a subsequent time period that is approximately equal to the threshold (140). The threshold may be determined by evaluating the foregoing recommendations based on clinical data over a number of diabetic patients that are provided by the AID algorithm or AP application, but can also be augmented by other considerations, such as a user's history of over-delivery or under-delivery, and the like. First, if the automated insulin delivery is more than the expected range of insulin dosage distributions which result in optimal glucose control behavior, the open-loop basal recommendation may be limited, for example, to approximately 70% of the user's total insulin delivery during automated mode. For example, an expected range of insulin dosage distributions that provide a user with near optimal glucose control may be approximately 25% to approximately 75% of a user's total daily insulin (TDI) as automated delivery. These variations be caused by variations in the user's insulin needs over time, or variations in the user's behaviors over time. A user may have dietary habits that result in their basal insulin needs to be significantly varying from the typical ideal distributions of 50% of their TDI, such as having a keto (low CHO) diet which would bias the distribution to a higher proportion, or ingesting much larger CHO amounts than the norm, which would bias the distribution to a lower proportion. In addition, the user may not bolus for a majority of their bolus needs, resulting in an automated delivery system compensating from bolus needs as part of increased basal delivery. In this case, although the automated insulin delivery's basal coverage may compose a greater proportion than 50% of their TDI, the user's actual basal insulin needs would not exceed 50% of their TDI.

Based on these ranges, the open-loop basal recommendation can be limited, for example, to approximately 70% of the user's total insulin delivered by the automated mode, as in FIGS. 3A and 3B. This approximate 70% threshold may also be varied depending on each user's estimated activity level, where users that indicate longer and/or more intense activity levels may limit this insulin delivery to a lower threshold, such as approximately 60%, and users that indicate a less intense activity level may allow this delivery to be provided at a higher threshold, e.g., approximately 75%. Here, although automated insulin delivery averaged 1.24 U/hour (hr), automated delivery also accounted for 29.85/

(12+29.85) or 71.3% of the user's total insulin delivery. The automated mode may be considered an open-loop basal recommendation. This open-loop basal recommendation may either be automatically programmed or may be a set of values that may be manually entered by the user to ensure a second layer of security.

For example, the processor may use the following equation to determine an average basal dosage to be delivered over the predetermined time period: $(0.7*(12+29.85 \text{ U}))/24=1.22$ U as an average that is less than a threshold, where 0.7 is the threshold, 12 U is the total amount of insulin delivered by bolus dosages at mealtimes, 29.85 U is the total amount of insulin delivered as basal dosages by the AID system and the value 24 is the number of hours in the predetermined time period. The AVG value may be considered a modified basal dosage value. This example shows that if the user's split in insulin needs are indicated to be significantly different from the typical 50/50 ratio, the proposed threshold only adjusts the total amount up to the threshold. This example illustrates practical application of 70% example threshold. So, in cases in which a user's basal/bolus split is 75%/25%, for example, the adjustment may only be modified up to 70% in this example. Of course, other thresholds may be used depending upon a user's specific physiology.

An instruction may be generated by the processor to deliver the modified basal dosage that substantially maintains the average basal dosage over the subsequent time period (150). At 160, the instruction may be output to cause an actuation of a pump mechanism of a wearable drug delivery device to deliver the modified basal dosage. The modified basal dosage may be delivered hourly with a predetermined start time based on, for example, a start time of the immediately previous basal dosage (e.g., the basal dosage delivered at 1 hour since midnight, if the current time is 2 hours since midnight). The modified basal dosage may also be delivered at a ramping rate over a variable duration (e.g. from 1 minute to 3 hours) based on a difference between the dosages, from the initial basal dosage to the modified basal dosage, to attempt to substantially match the body's continuous transition between states of varying insulin needs. Of course, other timing schemes for delivery of the modified basal dosage may be used to satisfy delivery of the average basal dosage over the predetermined time period.

Additional steps may be applied or included in the process 100. For example, with reference to the example process 100 of FIG. 1 at step 150, the processor may be further operable to determine a modified basal dosage using the average basal dosage for delivery at a particular time within the predetermining period of time.

Alternatively, in another example, the recommended basal dosage may be either reduced by the modification value or increased by the modification value to be approximately equal to the average basal dosage, wherein the modification value is a value that is either added or subtracted from the recommended basal dosage. For example, the processor may determine the modified basal dosage by determining a modification value that is based on the average basal dosage. For example, the modification value may be −0.02 U/24 hours, +0.02 U/24 hours, or the like. The modification value may be applied to a recommended basal dosage to be administered during a subsequent time period. For example, in FIGS. 3A and 3B, the automated amount of insulin delivered as a recommended dosage by the AP application or AID algorithm was equal to 29.85 U of insulin, which accounts for 1.24 U/hour of the 24 hours of the predetermined time period. However, after applying (in this example, subtracting) the modification value from the recommended basal dosage (i.e., 1.24−0.02=1.22), the modified basal dosage may be 1.22 U/hr. The subsequent period of time may, for example, be equal to the predetermined time period. In other examples, the subsequent period of time may be shorter or longer than the predetermined time period. This assessment may then be repeated after each increment of the predetermined period to adapt to changes in the user's insulin needs over time.

Alternatively, in another example, the recommended basal dosage may be modified by a modification coefficient. The modification coefficient may be applied to the recommended basal dosage to provide the modified basal dosage, which may be approximately equal to the average basal dosage. Application of the modification coefficient may be by a multiplication or division operation.

For example, the processor, when executing the programming code to determine the modified basal dosage, may be further operable to generate a modification coefficient determined based on the average basal dosage. The example may also include a step in which a recommended basal dosage to be administered during the subsequent time period may be multiplied by the modification coefficient to produce the modified basal dosage. For example, the modification coefficient may be 0.1, 0.5, 1.0, 1.5, 2, 3, or the like, which may be representative of a percentage to reduce (or increase) the basal dosage amount. Using the values in FIG. 3B, the recommended basal dosage may be 1.24 U/hour, and the modified basal dosage may be determined by applying a modification of 0.98 to the recommended basal dosage of 1.24 U/hour (i.e., 0.98*1.24=approximately 1.22).

Figure 4A:
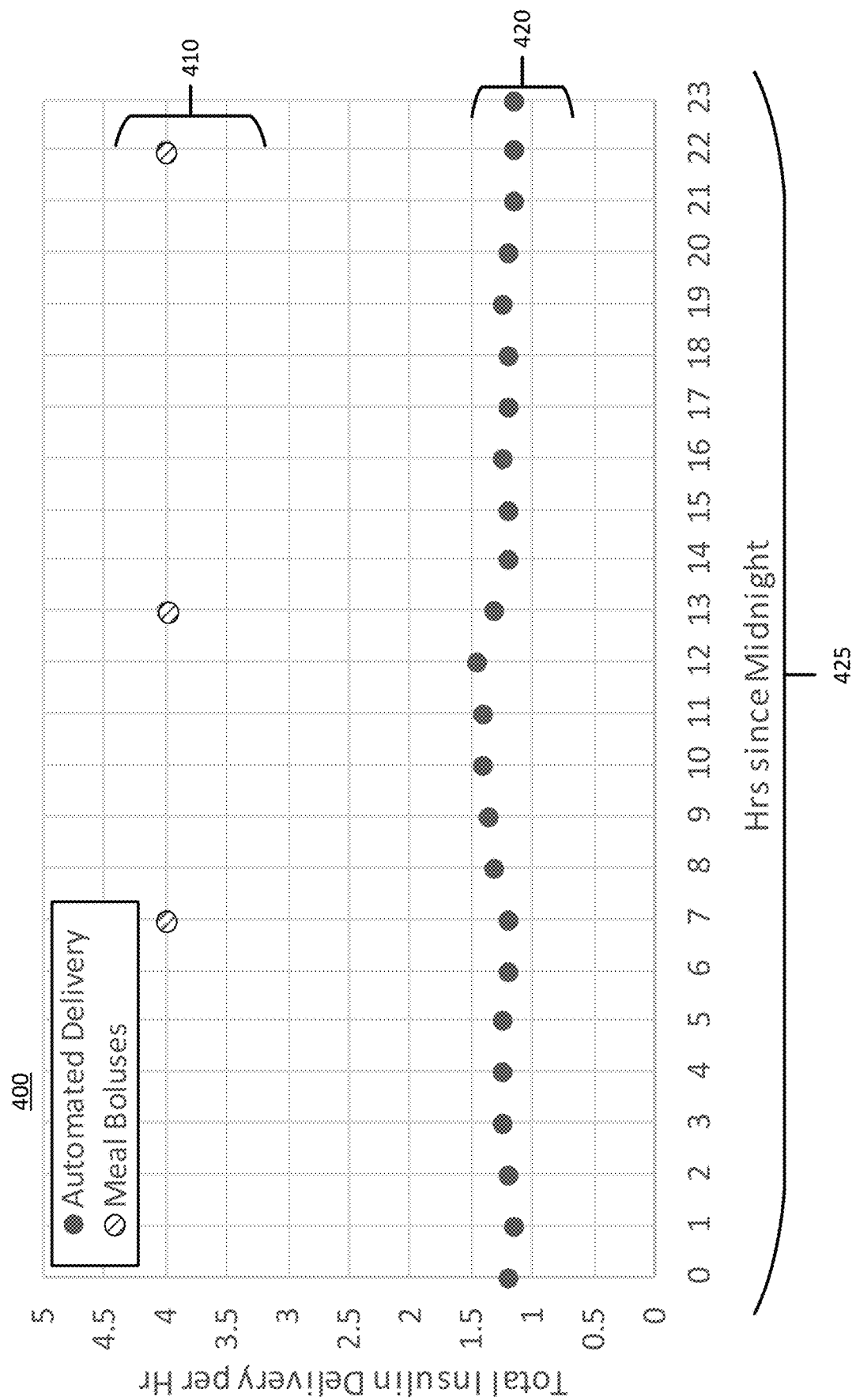
FIG. 4A illustrates another example of basal insulin dosages delivered over a predetermined time period.

In a further example with reference to the graph 400 of FIG. 4A, the AID system may be operable to deliver recommended basal dosages 420 over the course of a predetermined time period 425 and also keep track of times when bolus dosages 410 have been administered. In the further example, the processor may disregard the contribution of basal dosages delivered in close proximity to the delivered bolus dosages. For example, bolus dosages may take some time, such as 90 minutes to 2 hours, or longer in some users, to be processed by the user's body during this post-bolus time period. This delay can have various effects on a user's blood glucose measurements. For example, due to the delay in processing the bolus dosages, the effect of the bolus dosage may not be readily detectable in the blood glucose measurement values received from a continuous blood glucose measurement device, and/or the AID algorithm or AP application may not have accurate information to formulate a basal dosage recommendation.

Figure 4B:
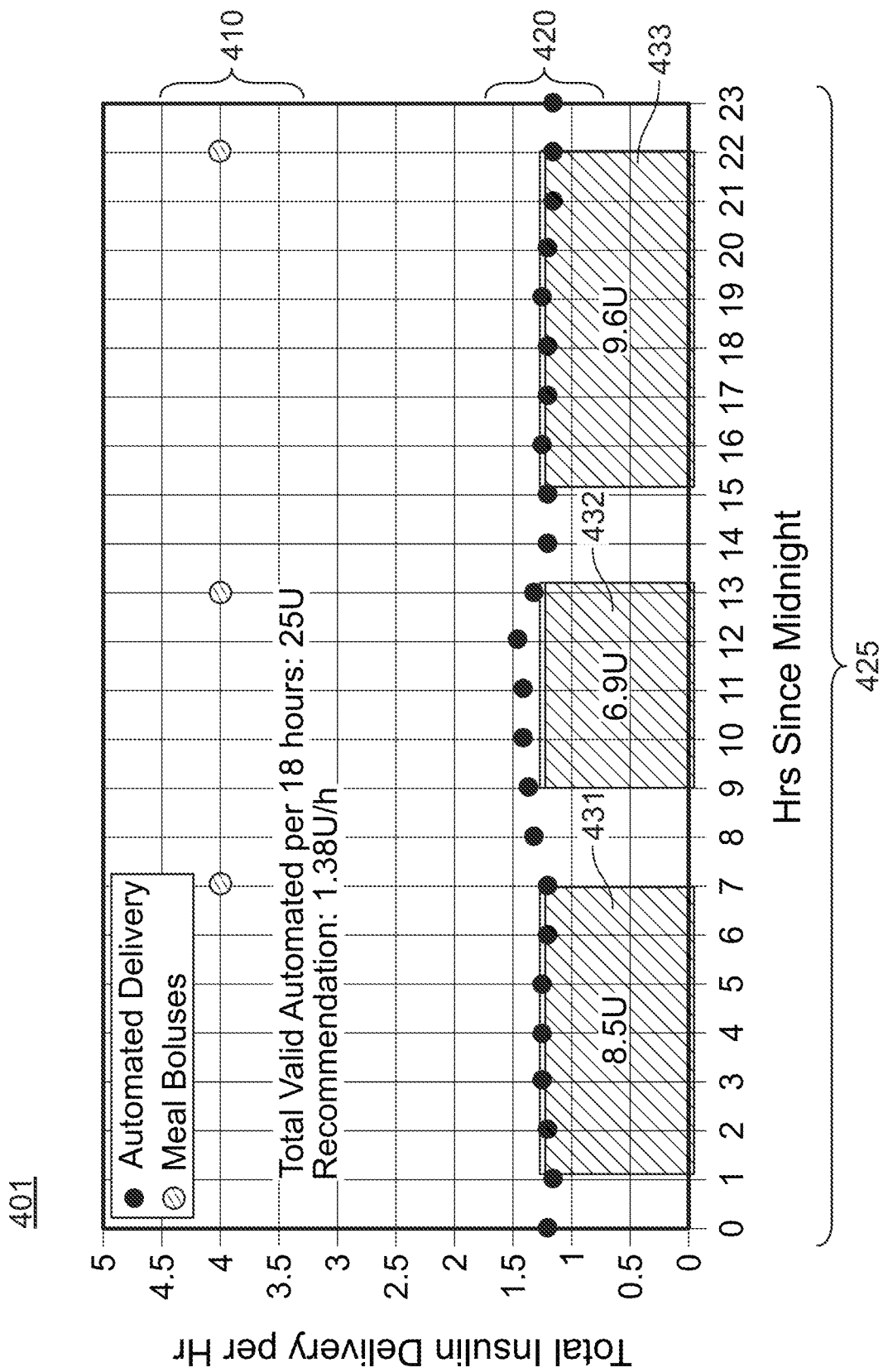
FIG. 4B illustrates a further example of a segmentation of a predetermined time period of FIG. 4A and an indication of an average basal insulin dosages determined for segments within the predetermined time period.

In this example of FIGS. 4A and 4B, the processor when executing programming code for implementing the process 100 may be operable to omit amounts of insulin delivered via the bolus dosages and any basal dosages delivered within the post-bolus time period. In the example of FIG. 4B, the insulin delivered in a two-hour period (e.g., the white windows between the time segments 431, 432 and 433 (grey regions)) after each meal during the predetermined time period 425 may be omitted from the calculation of an optimal dosage. As explained below, the AP application or AID algorithm may only consider the amount of insulin delivered during the respective time segments 431, 432, and 433 for inclusion in the total amount of insulin delivered to the user over the entire predetermined time period 425.

In the example of FIGS. 4A and 4B, the total amount of insulin provided by bolus dosages may be 12 U. As shown in the graph 401 of FIG. 4B, the amount of insulin delivered during a first segment 431 of the predetermined time period may, for example, be equal to 8.5 U. The amount of insulin delivered during a second segment 432 of the predetermined time period may, for example, be equal to 6.9 U, and the amount of insulin delivered during a third segment 433 of the predetermined time period may, for example, be equal to 9.6 U.

The process 100 may be implemented by a processor that is operable to utilize the values from the predetermined time period to determine a modified basal dosage. The total amount of insulin provided by basal dosages (minus any basal dosages delivered during the post-bolus time period) may be equal to 25 U (i.e., 8.5 (from first segment 431)+6.9 (from second segment 432)+9.6 (from third segment 433)). The calculation performed by the processor may be 12 U+25 U (=37 U) to determine the total amount of insulin delivered (i.e., 37 U) during the predetermined time period 425. The processor may be operable to determine the proportion of the total amount of insulin that was delivered via the basal dosages, but dividing 25 U (i.e., the total amount of insulin delivered by basal dosages) by the total amount of insulin delivered (i.e., 37 U) during the predetermined time period 425. The quotient of the division is 0.6756, which is compared to the threshold. For example, if the threshold is 0.70, the amount of basal dosages is below the threshold and therefore, closer to the 50-50 distribution of basal dosages to bolus dosages. In the example, the recommended basal dosage may be calculated as 25 U/24 hours or 1.38 U/hr. The example of FIGS. 4A and 4B illustrate that the modified basal dosage for the subsequent time period does not have to be different from that of the earlier predetermined time period from which the modified basal dosage is determined.

As shown in FIG. 4B, the processor may, in this example, be operable to divide the predetermined time period 425 into segments of time. In the example, the subsequent period of time may correspond to one segment of the segments of time, and the processor when executing the programming code is further operable when determining the average basal dosage to be delivered within the subsequent time period to select one segment of time from the predetermined time period, such as hours 1-7, hours 7-10, hours 9-13 or hours 15-22, or the like. The processor may sum an amount of insulin delivered as the basal dosages in the selected one segment of time; and divide the sum of the amount of insulin by a number of hours in the one segment of time to calculate the average basal dosage.

In an example, the process 100 may be operable to communicatively couple with a wearable drug delivery device. The processor may output a control signal including the instruction for receipt by a controller of the wearable drug delivery device to actuate the pump mechanism to administer insulin according to the modified basal dosage.

A user insulin delivery history of insulin delivered to a user may be maintained by the processor. Note that the phrase "delivered to the user" may also refer to the output of insulin from a reservoir in response to a control signal from a processor to actuate a pump mechanism, rather than the control signal itself, which may be relevant in cases where the actual insulin delivery may be a modified amount compared to the processor's outputs. The user insulin delivery history may include amounts of insulin delivered to the user in basal dosages and bolus dosages over a predetermined time period. Alternatively, or in addition, the user insulin delivery history may include data from a plurality of predetermined time periods and the data includes each basal delivery dosage, a respective time of when each respective basal delivery dosage was delivered within a respective predetermined time period of the plurality of predetermined time periods. In one example, the user insulin delivery history may refer to basal delivery dosages and/or bolus dosages recommended to be delivered by the AID algorithm or AP application. In another example, the user insulin delivery history may refer to basal delivery dosages and/or bolus doses actually output from the reservoir. In yet another example, the user insulin delivery history may refer to basal delivery dosages and/or bolus dosages that are both recommended to be delivered by the AID algorithm or AP application and the basal delivery dosages and/or bolus dosages actually output from the reservoir.

In the example, a basal dosage may be delivered more often over the predetermined time period than a bolus dosage, and the bolus dosage may include a greater amount of insulin than a basal dosage. In the example, prior to when the processor is determining a total amount of insulin delivered to the user, the processor may be operable to retrieve the total basal dosage amount of insulin delivered in the basal dosages over the predetermined time period from the user insulin delivery history. The processor may also retrieve the total basal dosage amount of insulin delivered in the basal dosages over the predetermined time period from the user insulin deliver history.

Figure 5A:
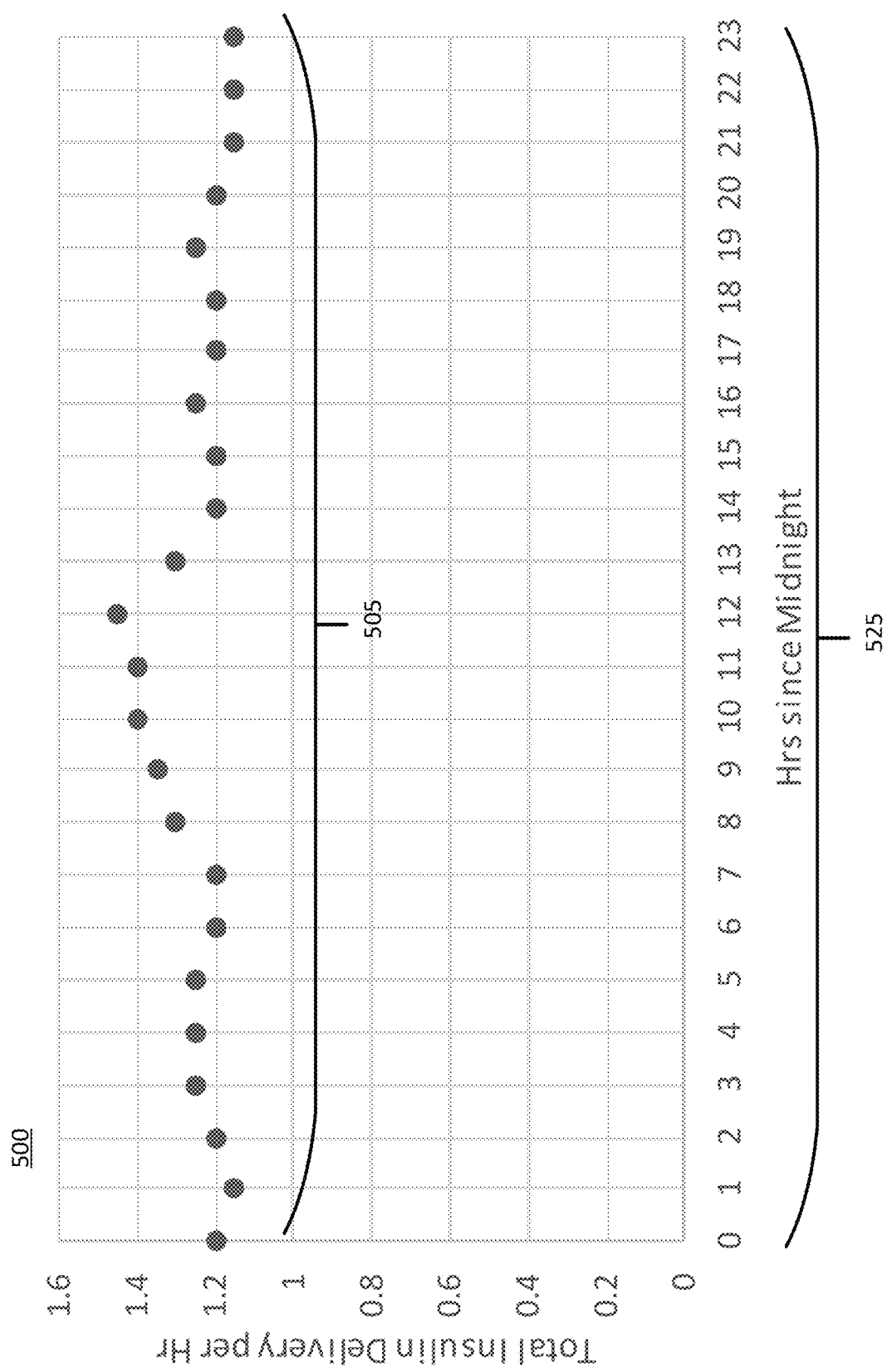
FIG. 5A illustrates an example of basal insulin dosages delivered over a predetermined time period.
Figure 5B:
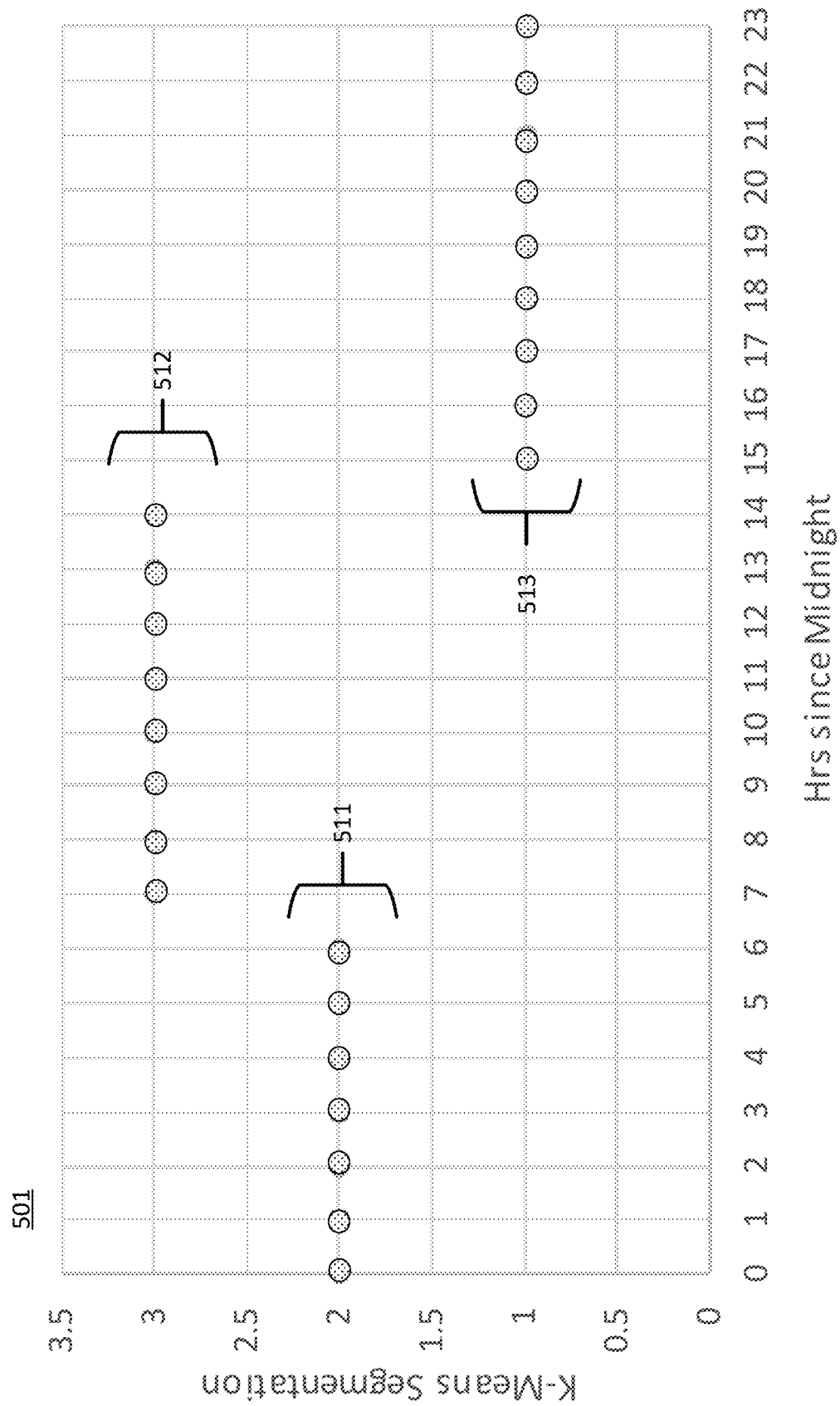
FIG. 5B illustrates an example of results of a clustering algorithm applied to the basal insulin dosages delivered over a predetermined time period of the example of FIG. 4A.
Figure 5C:
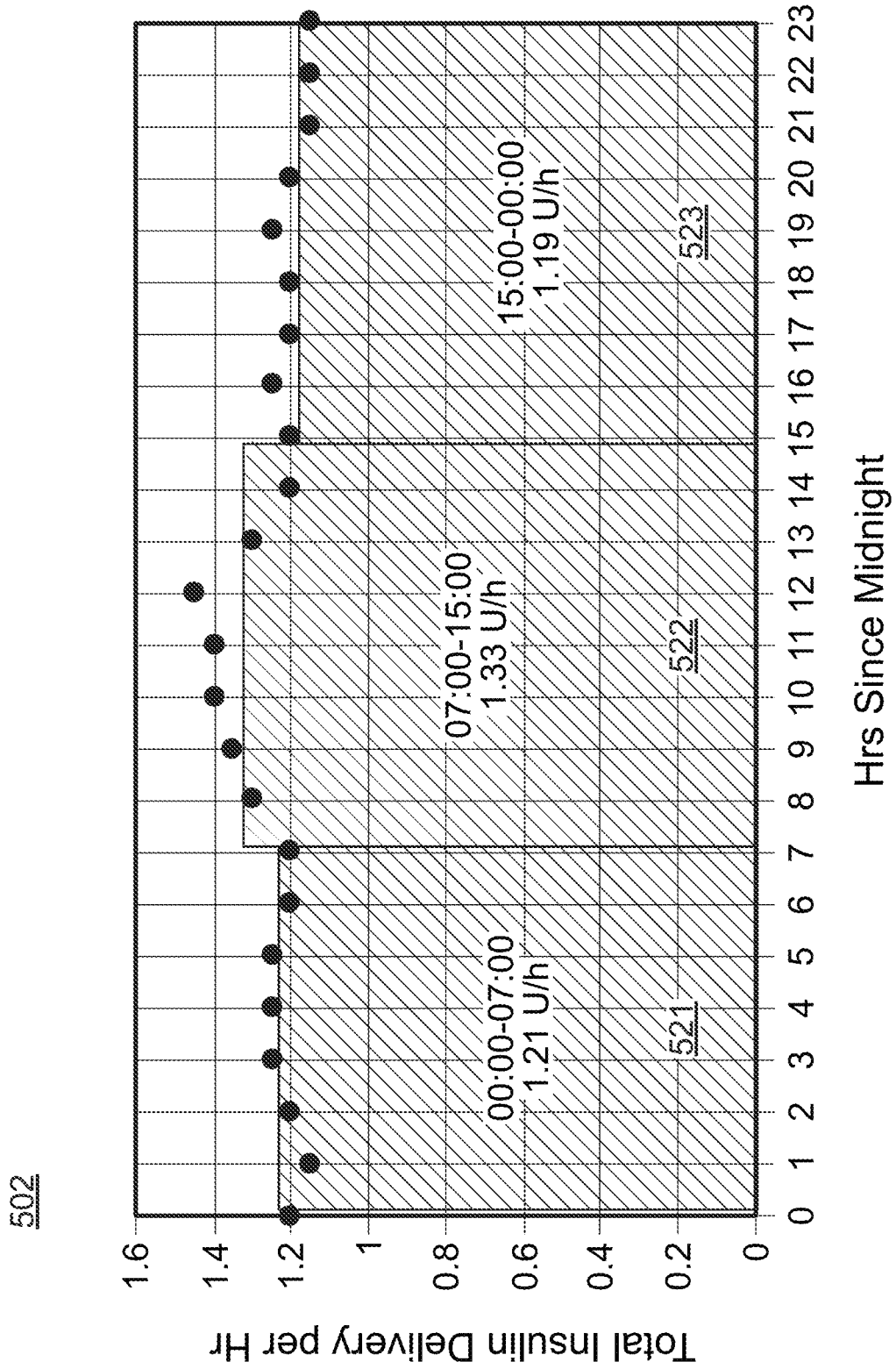
FIG. 5C illustrates an example of determining modified basal dosages according to examples of FIGS. 5A and 5B.

In contrast to other examples that may provide a single manual basal delivery recommendation to the user, time of day and clustering algorithms can be used to determine basal delivery profiles on an hourly basis, as shown in FIGS. 5A-5C.

For example, the processor may access a user insulin delivery history that may include data from a plurality of predetermined time periods. The data may include each basal delivery dosage, a respective time of when each respective basal delivery dosage was delivered within a respective predetermined time period of a number of predetermined time periods. Using the retrieved total basal dosage amount of insulin delivered in basal dosages, the processor may apply a clustering algorithm to the data from each of a number of predetermined time periods. For example, in the graph 500 of FIG. 5A, the individual basal dosages 505 are delivered during each hour of the day, which makes up the predetermined time period 525. In the example, the predetermined time period 525 may be divided into segments of time, such as hours or minutes. The basal dosages may be delivered or administered within non-uniform segments of the predetermined time period 525. As shown in graph 501 of FIG. 5B, the processor, upon application of the clustering application, may be operable to obtain a number of segments of a predetermined time period. The clustering algorithm may determine basal delivery profiles on an hourly basis. For example, the respective basal dosage deliveries may be clustered according to the respective delivery times. In FIG. 5B, the seven hours since midnight may be clustered around a K-means segmentation value of 2 as shown by 511. A next 8 hours after those in 511 may be clustered around a K-means segmentation value of 3 as shown by 512. The remaining 9 hours of the 24 hours since midnight may be clustered around a K-means segmentation value of 1 as shown by 513. Each respective segment of the number of segments may include a respective average basal dosage for the respective segment. The processor may be operable to determine a segment modified basal dosage to be delivered during a corresponding segment in a subsequent time period as the modified basal dosage. For example, as shown in the example of FIGS. 5A-5C, a predetermined time period extends for a 24-hour period of time from 0 hours after midnight to 23 hours after midnight.

In an example, the segment modified basal dosage may delivered in uniform (e.g., 8 hour intervals, 6 hour intervals, 3 hour intervals or the like) or non-uniform segments of the subsequent time period (e.g., typical sleeping hours versus typical awake hours for a respective user, or the like).

As shown in graph 502 of FIG. 5C, the result of the clustering may indicate these respective times, such as hours 0-6 after midnight are used by the AID algorithm or the AP application are to be grouped together in first clustering group 521 to provide a first recommended basal dosage value, such as 1.21 U/hr. The second clustering group 522 may indicate a second grouping of respective times, such as hours 7-15 be grouped together to provide a second recommended basal dosage value, such as 1.33 U/hr. The third clustering group 523 may indicate a third grouping of respective times, such as hours 16-00 be grouped together to provide a third recommended basal dosage value, such as 1.19 U/hr.

In the examples of FIGS. 1 and 3A-5C, the example processes may be implemented by programming code, such as an AP application or AID application, that is executed by a processor. The AP application or the AID application when executed by a processor may utilize inputs and calculations as described with respect to the foregoing examples.

It may be helpful to discuss an example of a drug delivery system that may implement the process example of FIGS. 1 and 3A-5C. FIG. 2 illustrates an example of a drug delivery system suitable for implementing the example processes and techniques described herein including those described with reference to FIGS. 1 and 3A-5C. Details of an example of a personal diabetes management device operable to establish settings for an automatic insulin delivery device, which may be a wearable drug delivery device, a delivery device, such as an OmniPod® System provided by Insulet Corp, or the like, are described with reference to the example system of FIG. 2.

The drug delivery system 200 may be operable to implement the process examples illustrated in and described with reference to FIGS. 1 and 3A-5C by executing an AP application or an AID algorithm. In an operational example, the drug delivery system 200 may be operable to attain information associated with a user. The AP application or an AID algorithm may be operable to determine a total amount of insulin delivered to the user over the predetermined time period. The total amount of insulin may be a sum of a total basal dosage amount of insulin delivered in the basal dosages over the predetermined time period and a total bolus dosage amount of insulin delivered in the bolus dosages over the predetermined time period. A proportion of the total amount of insulin delivered to the user provided via the total basal dosage amount over the predetermined time period may be determined. The processor may determine whether the proportion of the total amount of insulin attributed to the total basal dosage amount of insulin exceeds a threshold. In response to determining the threshold is exceeded, an average basal dosage to be delivered within a subsequent time period that is approximately equal to the threshold may be determined. An instruction may be generated to deliver a modified basal dosage that substantially maintains the average basal dosage over the subsequent time period. The instruction may be output to cause an actuation of a pump mechanism 224 of a wearable drug delivery device 202 to deliver the modified basal dosage.

In addition, further considerations may be implemented in terms of the safety of this recommendation as additions to the proportion of total basal deliveries during automated delivery. For instance, the system 200 may review the user's actual glucose control performance based on information provided by a sensor 204 and find that the user experiences a significantly increased time in hypoglycemic range at certain hours of the day. In response, the PDM device 206 may be operable to revise the limit to the maximum recommended basal proportion of the user's total daily insulin (TDI). For example, the response may be for the AP application to reduce the maximum recommended basal proportion to a lower value for improved user safety. For instance, if the user's glucose control performance shows a percent (%) of time per day in hypoglycemic range (<70 mg/dL glucose reading) of greater than a certain percentage of time, e.g. >10%, then the described system may reduce a user's maximum daily basal proportion to a lower value (e.g. 55%) than the original limit (e.g. 75%). In an example, this lower value can be made dependent on the percentage of time in the hypoglycemic range, e.g. if the user's percentage (%) of time in the hypoglycemic range is 2.5%, the system may reduce the original limit by 5%, whereas if the user's percentage of time in the hypoglycemic range is 5%, the original limit may be reduced by 10%, and so on. As such, the system may apply the following exemplary equation: Reduction of user's maximum daily basal proportion=2*user's percentage of time in hypoglycemic range.

The drug delivery system 200 may be an automatic drug delivery system that may include a wearable drug delivery device 202 (also referred to as "a drug delivery device," a medical device," or "a delivery device,"), a blood glucose sensor 204 (also referred to as "a continuous glucose monitor" or "a blood glucose measurement device"), and a personal diabetes management device (PDM) 206. The system 200, in an example, may also include a smart device 207, which may be operable to communicate with the PDM device 206 and/or other components of system 200 either via a wired or wireless communication link, such as 291, 292 or 293. In a specific example, the smart device 207 may only be coupled to the PDM device 206 via a wireless communication link 293, which may be a wireless communication link that utilizes the Bluetooth communication protocol, or the like.

In an example, the wearable drug delivery device 202 may be attached to the body of a user, such as a patient or diabetic, and may deliver any therapeutic agent, including any drug or medicine, such as insulin, morphine, or the like, to the user. The wearable drug delivery device 202 may, for example, be a wearable device worn by the user. For example, the wearable drug delivery device 202 may be directly coupled to a user (e.g., directly attached to a body part and/or skin of the user via an adhesive or the like). In an example, a surface of the wearable drug delivery device 202 may include an adhesive (not shown) to facilitate attachment to a user.

The wearable drug delivery device 202 may include a number of components to facilitate automatic delivery of a drug (also referred to as a therapeutic agent) to the user. The wearable drug delivery device 202 may be operable to store the drug (e.g., insulin) and to provide the drug to the user. The wearable drug delivery device 202 is often referred to as a pump, or an insulin pump, in reference to the operation of expelling insulin from the reservoir 225 for delivery to the user. While the examples refer to the reservoir 225 storing insulin, the reservoir 225 may be operable to store other drugs or therapeutic agents, such as morphine, or the like, that are suitable for automatic delivery.

In various examples, the wearable drug delivery device 202 may be an automatic, wearable drug delivery device.

For example, the wearable drug delivery device 202 may include a reservoir 225 for storing the drug (such as insulin), a needle or cannula (not shown) for delivering the drug into the body of the user (which may be done subcutaneously, intraperitoneally, or intravenously), and a pump mechanism (mech.) 224, or other drive mechanism, for transferring the drug from the reservoir 225, through a needle or cannula (not shown), and into the user. The pump mechanism 224 may be fluidly coupled to reservoir 225, and communicatively coupled to the controller 221 of the wearable drug delivery device 202. The wearable drug delivery device 202 may also include a power source 228, such as a battery, a piezoelectric device, or the like, for supplying electrical power to the pump mechanism 224 and/or other components (such as the controller 221, memory 223, and the communication device 226) of the wearable drug delivery device 202. Although not shown, an electrical power supply for supplying electrical power may similarly be included in each of the sensor 204, the smart device 207 and the PDM device 206.

The blood glucose sensor 204 may be a device communicatively coupled to the PDM processor 261 or controller 221 and may be operable to measure a blood glucose value at a predetermined time interval, such as every 5 minutes, or the like. The blood glucose sensor 204 may provide a number of blood glucose measurement values to the AP applications (e.g., 229, 249, 269, or 279) operating on the respective devices (e.g., 202, 204, 206, or 207). While the AP applications 229, 249, 269 and 279 were discussed in detail and shown in the system 200 example of FIG. 2, the AP applications 229, 249, 269 and 279 may be replaced with an AID algorithm that is also operable to control and communicate with connected devices, such as wearable drug delivery device 202 and sensor 204, and manage a personal diabetes treatment program, and provide the functions and services as described herein.

In a further example, as shown in the example of FIG. 2, the processor 261 of the PDM device 206 may be operable to communicatively couple with a continuous blood glucose sensor, such as blood glucose sensor 204. For example, the continuous blood glucose sensor may be the same as or similar to the blood glucose sensor 204 shown in a later example and the processor, via a wireless communication device executing the process 100, may be operable to establish, for example, a Bluetooth® connection with a continuous blood glucose sensor. In the example, the processor 261 may receive blood glucose measurement values via the wireless communication device from the continuous blood glucose sensor. The PDM processor 261 may be operable to use the received blood glucose measurement values to determine a recommended basal dosage to be administered during the subsequent time period. In some examples, due to some settings in the AID algorithm or AP application, the recommended basal dosage may not be a correct basal dosage to comply with the even distribution (e.g., 50-50) of basal dosage and bolus dosage to deliver the total amount of insulin for the predetermined time period. The processor may be operable to modify the recommended basal dosage to provide a modified basal dosage according to the process 100.

The wearable drug delivery device 202 may provide the insulin stored in reservoir 225 to the user based on information (e.g., blood glucose measurement values, predicted future blood glucose measurements, evaluations based on a user request for a bolus, a user interaction with PDM device 206, wearable drug delivery device 202, sensor 204 or smart device 207), evaluations of missing blood glucose measurements and the other information provided by the sensor 204, smart device 207, and/or the management device (PDM) 206. For example, the wearable drug delivery device 202 may contain analog and/or digital circuitry that may be implemented as a controller 221 for controlling the delivery of the drug or therapeutic agent. The circuitry used to implement the controller 221 may include discrete, specialized logic and/or components, an application-specific integrated circuit (ASIC), a microcontroller or processor that executes software instructions, firmware, programming instructions or programming code (enabling, for example, the artificial pancreas application (AP App) 229 as well as the process examples of FIGS. 1 and 2) stored in memory 223, or any combination thereof. For example, the controller 221 may execute a control algorithm, such as the artificial pancreas application 229, and other programming code that may make the controller 221 operable to cause the pump to deliver doses of the drug or therapeutic agent to a user at predetermined intervals or as needed to bring blood glucose measurement values to a target blood glucose value. In an example, the AP application (App) 229 may include programming code that is operable upon execution by the controller 221 to provide the example processes for adjusting or modifying total daily insulin settings, or the like as described with reference to FIGS. 1 and 2. The user preferences for total daily insulin settings may be programmed, for example, into an artificial pancreas application 229 by the user or by a third party (such as a health care provider, medical device manufacturer, or the like) using a wired or wireless link, such as 231, between the wearable drug delivery device 202 and a personal diabetes management device 206 or other device, such as a computing device at a healthcare provider facility. In an example, the pump or wearable drug delivery device 202 is communicatively coupled to the PDM processor 261 of the personal diabetes management device via the wireless link 231 or via a wireless link, such as 291 from smart device 207 or 208 from the sensor 204. The pump mechanism 224 of the wearable drug delivery device 202 may be operable to receive an actuation signal from the PDM processor 261, and in response to receiving a command signal or an actuation signal, expel insulin from the reservoir 225 based on the commands from an AP application, such as 269.

In an operational example, the AP application 269 executing in the personal diabetes management device 206 may be operable to control delivery of insulin to a user. For example, the AP application 269 may be operable to determine timing of an insulin dose and may output a command signal to the wearable drug delivery device 202 that actuates the pump mechanism 224 to deliver an insulin dose. In addition, the AP application (or AID algorithm) 269 when loaded with programmed code, provides instructions to carry out the functionality represented in FIGS. 1 and 2.

The other devices in the system 200, such as personal diabetes management device 206, smart device 207 and sensor 204, may also be operable to perform various functions including controlling the wearable drug delivery device 202. For example, the PDM device 206 may include a communication device 264, a PDM processor 261, and a personal diabetes management device memory 263. The personal diabetes management device memory 263 may store an instance of the AP application 269 that includes programming code, that when executed by the PDM processor 261 provides the process examples described with reference to the examples of FIGS. 1 and 2. The personal diabetes management device memory 263 may also store programming code for providing the process examples described with reference to the examples of FIGS. 1 and 2.

The smart device 207 may be, for example, a smart phone, an Apple Watch®, another wearable smart device, including eyeglasses, provided by other manufacturers, a global positioning system-enabled wearable, a wearable fitness device, smart clothing, or the like. Similar to the personal diabetes management device 206, the smart device 207 may also be operable to perform various functions including controlling the wearable drug delivery device 202. For example, the smart device 207 may include a communication device 274, a processor 271, and a memory 273. The memory 273 may store an instance of the AP application 279 and/or an instance of an AID application (not shown) that includes programming code for providing the process examples described with reference to the examples of FIGS. 1 and 4A-5C. The memory 273 may also store programming code and be operable to store data related to the AP application 279 or an instance of an AID algorithm (not shown). In an operational example, the AP application 279 may be operable to provide functionality similar to or the same functionality as described with reference to the instance of the AP application 269.

The sensor 204 of system 200 may be a continuous glucose monitor (CGM) as described above, that may include a processor 241, a memory 243, a sensing or measuring device 244, and a communication device 246. The memory 243 may, for example, store an instance of an AP application 249 as well as other programming code and be operable to store data related to the AP application 249 and process examples described with reference to FIGS. 1 and 2. The AP application 249 may also include programming code for providing the process examples described with reference to the examples of FIGS. 1 and 2.

Instructions for determining the delivery of the drug or therapeutic agent (e.g., as a bolus dosage) to the user (e.g., the size and/or timing of any doses of the drug or therapeutic agent) may originate locally by the wearable drug delivery device 202 or may originate remotely and be provided to the wearable drug delivery device 202. In an example of a local determination of drug or therapeutic agent delivery, programming instructions, such as an instance of the artificial pancreas application 229, stored in the memory 223 that is coupled to the wearable drug delivery device 202 may be used to make determinations by the wearable drug delivery device 202. In addition, the wearable drug delivery device 202 may be operable to communicate with the cloud-based services 211 via the communication device 226 and the wireless communication link 288. In an example, the system 200 may include one or more components operable to implement the process examples of FIGS. 1, 2, 4 and 5.

Alternatively, the remote instructions may be provided to the wearable drug delivery device 202 over a wired or wireless link (such as 231) by the personal diabetes management device (PDM) 206, which has a PDM processor 261 that executes an instance of the artificial pancreas application 269, or the smart device 207 (via wireless communication link 291), which has a processor 271 that executes an instance of the artificial pancreas application 269 as well as other programming code for controlling various devices, such as the wearable drug delivery device 202, smart device 207 and/or sensor 204. In an example, a message may be sent to a server, for example, in the cloud-based services 211 or the like, requesting downloading of the one or more clustering algorithms, a user's insulin delivery history, a user's blood glucose measurement value history, or the like to a personal diabetes management (PDM) 206 or smart device 207. The wearable drug delivery device 202 may execute any received instructions (originating internally or from the personal diabetes management device 206) for the delivery of the drug or therapeutic agent to the user. In this way, the delivery of the drug or therapeutic agent to a user may be automatic.

In various examples, the wearable drug delivery device 202 may communicate via a wireless link 231 with the personal diabetes management device 206. The personal diabetes management device 206 may be an electronic device such as, for example, a smart phone, a tablet, a dedicated diabetes therapy personal diabetes management device, or the like. The personal diabetes management device 206 may be a wearable wireless accessory device. The wireless links 208, 231, 232, 291, 292 and 293 may be any type of wireless link provided by any known wireless standard. As an example, the wireless links 208, 231, 232, 291, 292 and 293 may enable communications between the wearable drug delivery device 202, the personal diabetes management device 206 and sensor 204 based on, for example, Bluetooth®, Wi-Fi®, a near-field communication standard, a cellular standard, or any other wireless optical or radio-frequency protocol.

The sensor 204 may be a glucose sensor operable to measure blood glucose and output a blood glucose value or data that is representative of a blood glucose value. For example, the sensor 204 may be a glucose monitor or a continuous glucose monitor (CGM). The sensor 204 may include a processor 241, a memory 243, a sensing/measuring device 244, and communication device 246. The communication device 246 of sensor 204 may include one or more sensing elements, an electronic transmitter, receiver, and/or transceiver for communicating with the personal diabetes management device 206 over a wireless link 232 or with wearable drug delivery device 202 over the wireless link 208. The sensing/measuring device 244 may include one or more sensing elements, such as a glucose measurement, heart rate monitor, or the like. The processor 241 may include discrete, specialized logic and/or components, an application-specific integrated circuit, a microcontroller or processor that executes software instructions, firmware, programming instructions stored in memory (such as memory 243), or any combination thereof. For example, the memory 243 may store an instance of an AP application 249 that is executable by the processor 241.

Although the sensor 204 is depicted as separate from the wearable drug delivery device 202, in various examples, the sensor 204 and wearable drug delivery device 202 may be incorporated into the same unit. That is, in various examples, the sensor 204 may be a part of the wearable drug delivery device 202 and contained within the same housing of the wearable drug delivery device 202 (e.g., the sensor 304 may be positioned within or embedded within the wearable drug delivery device 202). Glucose monitoring data (e.g., measured blood glucose values) determined by the sensor 204 may be provided to the wearable drug delivery device 202, smart device 207 and/or the personal diabetes management device 206 and may be used to perform the functions and deliver doses of insulin for automatic delivery of insulin by the wearable drug delivery device 202 as described with reference to the examples of FIGS. 1 and 2.

The sensor 204 may also be coupled to the user by, for example, adhesive or the like and may provide information or data on one or more medical conditions and/or physical attributes of the user. The information or data provided by the sensor 204 may be used to adjust drug delivery operations of the wearable drug delivery device 202.

In an example, the personal diabetes management device 206 may be a mobile computing device operable to manage a personal diabetes treatment plan via an AP application or an AID algorithm. The personal diabetes management device 206 may be used to program or adjust operation of the wearable drug delivery device 202 and/or the sensor 204. The personal diabetes management device 206 may be any portable electronic, computing device including, for example, a dedicated controller, such as PDM processor 261, a smartphone, or a tablet. In an example, the personal diabetes management device (PDM) 206 may include a PDM processor 261, a personal diabetes management device memory 263, and a communication device 264. The personal diabetes management device 206 may contain analog and/or digital circuitry that may be implemented as a PDM processor 261 (or controller) for executing processes to manage a user's blood glucose levels and for controlling the delivery of the drug or therapeutic agent to the user. The PDM processor 261 may also be operable to execute programming code stored in the personal diabetes management device memory 263. For example, the personal diabetes management device memory 263 may be operable to store an artificial pancreas (AP) application 269 that may be executed by the PDM processor 261. The PDM processor 261, when executing the artificial pancreas application 269, may be operable to perform various functions, such as those described with respect to the examples in FIGS. 1 and 2. The wireless communication device 264 may be a device, such as a receiver, a transmitter, or a transceiver that operates according to one or more radio-frequency protocols. For example, the communication device 264 may include a cellular transceiver and a Bluetooth transceiver that enables the personal diabetes management device 206 to communicate with a data network (not shown) via the cellular transceiver and with the sensor 204 and the wearable drug delivery device 202. The respective transceivers of communication device 264 may be operable to transmit signals containing information useable by or generated by the AP application or the like. The communication devices 226, 246 and 276 of respective wearable drug delivery device 202, sensor 204 and smart device 207 may also be operable to transmit signals containing information useable by or generated by the AP application or the like.

The wearable drug delivery device 202 may communicate with the sensor 204 over a wireless link 208 and may communicate with the personal diabetes management device 206 over a wireless link 231. The sensor 204 and the personal diabetes management device 206 may communicate over a wireless link 232. The smart device 207, when present, may communicate with the wearable drug delivery device 202, the sensor 204 and the personal diabetes management device 206 over wireless links 291, 292 and 293, respectively. The wireless links 208, 231, 232, 291, 292 and 293 may be any type of wireless link operating using known wireless standards or proprietary standards. As an example, the wireless links 208, 231, 232, 291, 292 and 293 may provide communication links based on Bluetooth®, Wi-Fi, a near-field communication standard, a cellular standard, or any other wireless protocol via the respective communication devices 226, 246 and 264. As such, the wearable drug delivery device 202, the smart device 207, blood glucose sensor 204 and/or the personal diabetes management device 206 may be paired to one another using known pairing protocols and procedures that enable wireless communication between one or more of the devices 202, 204, 206 and 207. In some examples, the wearable drug delivery device 202 and/or the personal diabetes management device 206 may include a user interface 227, 278 and 268, respectively, such as a keypad, a touchscreen display, levers, buttons, a microphone, a speaker, a light, a display, or the like, that is operable to allow a user to enter information and allow the personal diabetes management device to output information for presentation to the user. Note that the respective user interface devices 227, 278 and 268 may serve with the associated hardware, such as a touchscreen display, as both an input device and an output device. For example, the user interface devices may present graphical user interfaces that guide a user, for example, through the presentation of prompts, to input information or provide data to the user as well as other functions.

In various examples, the drug delivery system 200 may implement the artificial pancreas (AP) algorithm (and/or provide AP functionality) to govern or control automatic delivery of insulin to a user (e.g., to maintain euglycemia—a normal level of glucose in the blood). The AP application (or an AID algorithm) may be implemented by the wearable drug delivery device 202 and/or the sensor 204. The AP application may be operable to determine an initial total daily insulin dosage as described with reference to the examples of FIGS. 1, 2, 4 and 5, as well as the times and incremental dosages of insulin delivery. In various examples, the AP application (or the AID algorithm) may determine the times and dosages for delivery based on information known about the user, such as the user's sex, age, weight, or height, and/or on information gathered about a physical attribute or condition of the user (e.g., from the sensor 204). For example, the AP application may determine an appropriate delivery of insulin based on glucose level monitoring of the user through the sensor 204. The AP application may also allow the user to adjust insulin delivery. For example, the AP application may allow the user to issue (e.g., via an input) commands to the wearable drug delivery device 202, such as a command to deliver an insulin bolus. In some examples, different functions of the AP application may be distributed among two or more of the personal diabetes management device 206, the wearable drug delivery device 202 or the sensor 204. In other examples, the different functions of the AP application may be performed by one device, such as the personal diabetes management device 206, the wearable drug delivery device 202 or the sensor 204.

As described herein, the drug delivery system 200 or any component thereof, such as the wearable drug delivery device 202 may be considered to provide AP functionality or to implement an AP application. Accordingly, references to the AP application (e.g., functionality, operations, or capabilities thereof) are made for convenience and may refer to and/or include operations and/or functionalities of the drug delivery system 200 or any constituent component thereof (e.g., the wearable drug delivery device 202 and/or the personal diabetes management device 206). The drug delivery system 200—for example, as an insulin delivery system implementing an AP application—may be considered to be a drug delivery system or an AP application-based delivery system that uses sensor inputs (e.g., data collected by the sensor 204).

In an example, one or more of the devices, 202, 204, 206 or 207 may be operable to communicate via a wireless communication link 288 with cloud-based services 211. The cloud-based services 211 may utilize servers and data storage (not shown). The communication link 288 may be a cellular link, a Wi-Fi link, a Bluetooth link, or a combination thereof, that is established between the respective devices 202, 204, 206 or 207 of system 200. The data storage provided by the cloud-based services 211 may store insulin delivery history related to the user, cost function data related to general delivery of insulin to users, or the like. In addition, the cloud-based services 211 may process anonymized data from multiple users to provide generalized information related to the various parameters used by the AP application.

In an example, the wearable drug delivery device 202 includes a communication device 264, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 211. For example, outputs from the sensor 204 or the wearable drug delivery device 202 may be transmitted to the cloud-based services 211 for storage or processing via the transceivers of communication device 264. Similarly, wearable drug delivery device 202, personal diabetes management device 206 and sensor 204 may be operable to communicate with the cloud-based services 211 via the communication link 288.

In an example, the respective receiver or transceiver of each respective device, 202, 206 or 207, may be operable to receive signals containing respective blood glucose measurement values of the number of blood glucose measurement values that may be transmitted by the sensor 204. The respective processor of each respective device 202, 206 or 207 may be operable to store each of the respective blood glucose measurement values in a respective memory, such as 223, 263 or 273. The respective blood glucose measurement values may be stored as data related to the artificial pancreas algorithm, such as 229, 249, 269 or 279. In a further example, the AP application operating on any of the personal diabetes management device 206, the smart device 207, or sensor 204 may be operable to transmit, via a transceiver implemented by a respective communication device, such as 264, 274, 246, a control signal for receipt by another medical device of the system 200. In the example, the control signal may indicate an amount of insulin to be expelled by the wearable drug delivery device 202.

Various operational scenarios and examples of processes performed by the system 200 are described herein. For example, the system 200 may be operable to implement the process examples of FIG. 1.

The techniques described herein for providing functionality to set an adjusted total daily insulin factor and determine whether the adjusted total daily insulin factor exceeds a maximum algorithm delivery threshold. In response to a result of the determination, set a total daily insulin dosage using the attained information and obtain blood glucose measurement values over a period of time. Based on the obtained blood glucose measurement values, a level of glycated hemoglobin of a user may be determined. The set total daily insulin dosage may be modified to provide a modified total daily insulin dosage in response to the determined level of glycated hemoglobin. A control signal including the modified total daily insulin dosage may be output instructing a controller to actuate delivery of insulin according to the modified total daily insulin dosage.

For example, the system 200 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

In addition, or alternatively, while the examples may have been described with reference to a closed loop algorithmic implementation, variations of the disclosed examples may be implemented to enable open loop use. The open loop implementations allow for use of different modalities of delivery of insulin such as smart pen, syringe or the like. For example, the disclosed AP application and algorithms may be operable to perform various functions related to open loop operations, such as the generation of prompts requesting the input of information such as weight or age. Similarly, a dosage amount of insulin may be received by the AP application or algorithm from a user via a user interface. Other open-loop actions may also be implemented by adjusting user settings or the like in an AP application or algorithm.

Some examples of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of non-transitory, machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A device, comprising:
a processor operable to execute programming code;
a memory coupled to the processor and operable to store the programming code; and
a wireless communication device operable to wirelessly communicate with a paired device and communicatively coupled to the processor;
wherein the programming code is executable by the processor, and the processor, when executing programming code, is operable to:
determine a total amount of insulin delivered to a user over a predetermined time period;
determine whether a proportion of the total amount of insulin attributed to a total basal dosage amount of insulin exceeds a threshold;
in response to determining the threshold is exceeded, determine an average basal dosage to be delivered within a subsequent time period that is approximately equal to the threshold; and
output an instruction to cause actuation of a pump mechanism of the paired device to deliver a modified basal dosage that substantially maintains the average basal dosage over the subsequent time period.

2. The device of claim 1, wherein the processor, when executing the programming code, is further operable to:
determine the modified basal dosage using the average basal dosage.

3. The device of claim 2, wherein the processor, when executing the programming code, is further operable when determining the modified basal dosage to:
determine a modification value that is based on the average basal dosage;
apply the modification value to a recommended basal dosage to be administered during the subsequent time period; and
include in the instruction an amount of insulin to be delivered that is approximately equal to the average basal dosage to be delivered as the modified basal dosage.

4. The device of claim 2, wherein the processor, when executing the programming code, is further operable when determining the modified basal dosage to:
generate a modification coefficient determined based on the average basal dosage; and
multiply a recommended basal dosage to be administered during the subsequent time period by the modification coefficient to produce the modified basal dosage.

5. The device of claim 1, wherein the processor, when executing the programming code, is further operable, when determining the total amount of insulin delivered to the user over the predetermined time period, to:
omit amounts of insulin delivered via bolus dosages and any basal dosages delivered within a preset period of time of delivery of each of the bolus dosages from being included in the total amount of insulin delivered to the user over the predetermined time period.

6. The device of claim 1, wherein the processor, when executing the programming code, is further operable to:
maintain a user insulin delivery history of insulin delivered to the user, wherein:
the user insulin delivery history includes amounts of insulin delivered to the user in basal dosages and bolus dosages over the predetermined time period,
a basal dosage is delivered more frequently over the predetermined time period than a bolus dosage, and
the bolus dosage includes a greater amount of insulin than the basal dosage; and
prior to when the processor is determining the total amount of insulin delivered to the user over the predetermined time period, the processor is further operable to perform functions to:
retrieve a total basal dosage amount of insulin delivered in the basal dosages over the predetermined time period from the user insulin delivery history; and
retrieve a total basal dosage amount of insulin delivered in the basal dosages over the predetermined time period from the user insulin delivery history.

7. The device of claim 6, wherein the processor, when executing the programming code, is further operable to:
access the user insulin delivery history, wherein the insulin delivery history includes data from a plurality of predetermined time periods and the data includes each basal delivery dosage, a respective time of when each respective basal delivery dosage was delivered within a respective predetermined time period of the plurality of predetermined time periods;

applying a clustering algorithm to the data from each of the plurality of predetermined time periods;

obtain a number of segments of the predetermined time period; and determine a segment modified basal dosage to be delivered during a corresponding segment in the subsequent time period as the modified basal dosage.

8. The device of claim 1, wherein:

the predetermined time period is divided into segments of time, the subsequent period of time corresponds to one segment of the segments of time, and the processor, when executing the programming code, is further operable when determining an average amount of insulin to be delivered within a subsequent time period to:

select one segment of time from the predetermined time period;

sum an amount of insulin delivered as the basal dosages in the selected one segment of time from the predetermined time period; and divide the sum of the amount of insulin by a number of hours in the selected one segment of time to calculate the average basal dosage for the subsequent period of time.

9. The device of claim 1, wherein:

the wireless communication device is operable to communicatively couple to a continuous blood glucose sensor;

the processor, when executing the programming code, is further operable to:

receive blood glucose measurement values via the wireless communication device from the continuous blood glucose sensor; and use the received blood glucose measurement values to determine a recommended basal dosage to be administered during the subsequent time period.

10. The device of claim 1, wherein:

the wireless communication device is operable to communicatively couple to a wearable drug delivery device; and the processor, when executing the programming code, is further operable to:

output a control signal including an instruction for receipt by a controller of the wearable drug delivery device to actuate the pump mechanism to administer insulin according to the modified basal dosage.

11. The device of claim 1, wherein the total amount of insulin is a sum of a total basal dosage amount of insulin delivered in basal dosages over the predetermined time period and a total bolus dosage amount of insulin delivered in bolus dosages over the predetermined time period.

12. The device of claim 1, wherein the processor, when executing the programming code, is further operable to:

determine a proportion of the total amount of insulin delivered to the user provided via the total basal dosage amount over the predetermined time period.

13. The device of claim 3, wherein the processor, when executing the programming code and applying the modification value, is further operable to:

add the modification value to the recommended basal dosage.

14. The device of claim 3, wherein the processor, when executing the programming code and applying the modification value, is further operable to:

subtract the modification value from the recommended basal dosage.

15. The device of claim 3, wherein the modification value is a modification coefficient, and the processor, when executing the programming code and applying the modification value, is further operable to:

multiply the recommended basal dosage by the modification value.

16. The device of claim 7, wherein each respective segment of the number of segments includes a respective average basal dosage for the respective segment.

17. The device of claim 1, wherein the wireless communication device is operable to receive signals from a glucose sensor.

* * * * *